US009238007B2

(12) United States Patent
Alles et al.

(10) Patent No.: US 9,238,007 B2
(45) Date of Patent: Jan. 19, 2016

(54) METHOD FOR THE PRODUCTION OF A MEDICAMENT CONTAINING TADALAFIL

(75) Inventors: Rainer Alles, Munich (DE); Julia Schulze Nahrup, Neuried (DE); Katrin Rimkus, Munich (DE)

(73) Assignee: RATIOPHARM GMBH, Ulm (DE)

( * ) Notice: Subject to any disclaimer, the term of this patent is extended or adjusted under 35 U.S.C. 154(b) by 873 days.

(21) Appl. No.: 12/665,309

(22) PCT Filed: Jun. 23, 2008

(86) PCT No.: PCT/EP2008/005066
§ 371 (c)(1),
(2), (4) Date: Mar. 26, 2010

(87) PCT Pub. No.: WO2009/000493
PCT Pub. Date: Dec. 31, 2008

(65) Prior Publication Data
US 2010/0179159 A1    Jul. 15, 2010

(30) Foreign Application Priority Data
Jun. 22, 2007 (DE) .......................... 10 2007 028 869

(51) Int. Cl.
A61K 31/4985 (2006.01)
A61K 31/495 (2006.01)
A61K 9/20 (2006.01)
A61K 9/14 (2006.01)

(52) U.S. Cl.
CPC ............. *A61K 9/2027* (2013.01); *A61K 9/146* (2013.01); *A61K 9/2031* (2013.01)

(58) Field of Classification Search
None
See application file for complete search history.

(56) References Cited

U.S. PATENT DOCUMENTS

| | | | |
|---|---|---|---|
| 4,108,996 A | 8/1978 | Lorincz et al. | |
| 4,343,789 A | 8/1982 | Kawata et al. | |
| 5,859,006 A | 1/1999 | Daugan | |
| 5,985,326 A | 11/1999 | Butler | |
| 6,140,329 A | 10/2000 | Daugan | |
| 6,548,490 B1 | 4/2003 | Doherty, Jr. et al. | |
| 6,821,975 B1 | 11/2004 | Anderson et al. | |
| 6,841,167 B1 | 1/2005 | Anderson et al. | |
| 6,943,166 B1 | 9/2005 | Pullman et al. | |
| 2003/0139384 A1 | 7/2003 | Dudley | |
| 2003/0211162 A1 | 11/2003 | Kerkhof | |
| 2003/0235617 A1 | 12/2003 | Martino et al. | |
| 2005/0019641 A1 | 1/2005 | Aoyama et al. | |
| 2005/0196418 A1 | 9/2005 | Yu et al. | |
| 2006/0099252 A1 | 5/2006 | Zalit et al. | |
| 2006/0127479 A1 | 6/2006 | Kumaraperumal et al. | |
| 2006/0276442 A1 | 12/2006 | Woodward | |
| 2006/0286166 A1* | 12/2006 | Ornan et al. ................. | 424/464 |
| 2007/0009589 A1 | 1/2007 | Raghupathi et al. | |
| 2008/0009502 A1 | 1/2008 | Zalit et al. | |
| 2008/0187588 A1* | 8/2008 | Zuleger et al. ................ | 424/469 |
| 2008/0226723 A1 | 9/2008 | Fritz et al. | |
| 2009/0004281 A1 | 1/2009 | Nghiem et al. | |
| 2009/0047330 A1 | 2/2009 | Bangalore | |
| 2009/0098211 A1 | 4/2009 | Zalit et al. | |
| 2010/0098211 A1 | 4/2010 | Hill et al. | |
| 2010/0297237 A1 | 11/2010 | Bloom et al. | |

FOREIGN PATENT DOCUMENTS

| | | | |
|---|---|---|---|
| CA | 2372025 A1 | 11/2000 | |
| CN | 1742732 | * | 3/2006 |
| CN | 1742732 A | 3/2006 | |
| EP | 0 297 866 | 4/1989 | |
| EP | 1 120 120 | 1/2001 | |
| EP | 1200091 | * | 2/2001 |
| EP | 1 269 994 | 1/2003 | |
| EP | 1 875 914 | 1/2008 | |
| WO | WO 94/28902 | 12/1994 | |
| WO | WO 95/19978 | 7/1995 | |
| WO | WO 96/16644 | 6/1996 | |
| WO | WO 96/38131 | 12/1996 | |
| WO | WO 97/03675 | 2/1997 | |
| WO | WO 00/66099 | 11/2000 | |
| WO | WO 01/08686 | 2/2001 | |
| WO | WO-01/08686 A1 | 2/2001 | |
| WO | WO 01/08687 | 2/2001 | |
| WO | WO 01/08688 | 2/2001 | |
| WO | WO 03/000343 | 1/2003 | |
| WO | WO-2004/037262 A2 | 5/2004 | |
| WO | WO-2005/000296 A1 | 1/2005 | |
| WO | WO-2005/065308 A2 | 7/2005 | |
| WO | WO 2005110420 | * | 11/2005 |
| WO | WO-2006/108519 A1 | 10/2006 | |
| WO | WO 2007/002125 | 1/2007 | |
| WO | WO 2008/005039 | 1/2008 | |
| WO | WO-2008/005039 A1 | 1/2008 | |
| WO | WO-2008/134557 A2 | 11/2008 | |
| WO | WO-2009/000493 A1 | 12/2008 | |
| WO | WO 2011/006596 | 1/2011 | |
| WO | WO-2011/006596 A2 | 1/2011 | |
| WO | WO 2011/012217 | 2/2011 | |
| WO | WO-2011/012217 A2 | 2/2011 | |

OTHER PUBLICATIONS

Leuner et al. (European Journal of Pharmaceutics and Biopharmaceutics 50, 47-60, 2000) Improving drug solubility for oral . . . .*

Cheng and Prusoff, Relationship Between the Inhibition constant ($K_i$) and the Concentration of Inhibitor Which Causes 50 Per Cent Inhibition ($I_{50}$) of an Enzymatic Reaction, *Biochem. Pharmacol.* 22:3099-3108 (1973).

(Continued)

*Primary Examiner* — Tigabu Kassa

(57) ABSTRACT

The invention relates to a method for producing a medicament containing tadalafil. In said method, tadalafil is mixed with suitable adjuvants and is heated to a temperature of about 100° C. to about 200° C., preferably about 150° C. to about 200° C., especially about 200° C.

8 Claims, No Drawings

(56) References Cited

OTHER PUBLICATIONS

Daugan et al., The Discovery of Tadalafil: A Novel and Highly Selective PDE5 Inhibitor. 2:2,3,6,7,12,12a-hexahydropyrazino [1',2':1,6]pyrido [3,4-b] indole-1,4-dione Analogues, J. Med. Chem. 46:4533-4542 (2003).
Galie et al., "Comparative Analysis of Clinical Trials and Evidence-Based Treatment Algorithm in Pulmonary Arterial Hypertension," J. Am. Coll. Cardiol 43( 12 Suppl. S) 81S-88S (2004).
Khan et al., "Controlled Release Copreciptitates: Formulation Considerations," *Journal of Controlled Release* 37:131-141 (1995).
Khan and Reddy., "Controlled Drug Delivery Development of Solid Oral Dosage Forms with Acrylate Polymers," *S.T.P. Pharma Sciences* 7:483-490 (1997).
Kislalioglu et al., "Physical Characterization and Dissolution Properties of Ibuprofen: Eudragit Coprecipitates," *J. Pharm Sci.* 80:799-804 (1991).
Specifications and Test Methods for EUDRAGIT® L 100 and EUDRAGIT® S 100, Deguessa. Creating Essentials, Info 7.3/E, Sep. 2004.
International Search Report from PCT/EP2010/004181, mailed Feb. 3, 2012.
Daugan A. et al., "The Discovery of Tadalafil: A Novel and Highly Selective PDE5 Inhibitor. 2: 2,3,6,7,12,12a-hexahydropyrazino[1',2':1,6]pyrido[3,4-b]indole-1,4-dione Analogues." *J Med Chem.* Oct. 9, 2003;46(21):4533-42.
Chinese Office Action for CN Application No. 200880021058.7 dated Mar. 3, 2011.
English Translation of Chinese Office Action for CN Application No. 200880021058.7 dated Mar. 3, 2011.
English Translation of excerpt from Reference D1, cited in Chinese Office Action for CN Application No. 200880021058.7 dated Mar. 3, 2011.
Ansel et al., Dosage Form Design: General Considerations, Pharmaceutic Ingredients, and Current Good Manufacturing Practice. *Pharmaceutical Dosage Forms and Drug Delivery Systems*, 6th Edition. Williams & Wilkins, 105-108 (1995).
Dissolution. *Remington: The Science and Practice of Pharmacy*, 20th Edition. Alfonso R. Gennaro, 656-657 (2000).
Eli Lilly and Company, "Cialis Prescribing Information," <http://pi.lilly.com/us/cialis-pi.pdf>, 2003 (revised 2009).
Finholt et al., "Effect of Different Factors on Dissolution Rate of Drugs from Powders, Granules and Tablets II," Meddelelser Norsk Farmaceutisk Selskap. 28(1):238-52 (1966).
Guidance for Industry: Food-Effect Bioavailability and Fed Bioequivalence Studies, 11 pages (2002).
International Search Report for International Application No. PCT/US2006/043664, dated Mar. 14, 2007 (3 pages).
International Search Report for International Application No. PCT/US2008/061638, dated Dec. 12, 2008 (3 pages).
Levy et al., "Effect on Certain Tablet Formulation Factors on Dissolution Rate of Active Ingredient II", J Pharm Sci. 52(11):1047-51 (1963).
Official Monograph of the National Formulary, United States Pharmacopeia & National Formulary, 2003, p. 2843, U.S. Pharmacopeial Convention, Inc., Rockville, MD.
Perry et al., Pneumatic-Conveyor Dryers and Spray Dryers. *Perry's Chemical Engineers' Handbook*, 6th Edition. McGraw-Hill Book Company, 51-58 (1984).
Starch. *Handbook of Pharmaceutical Excipients*, 4th Edition. Pharmaceutical Press, Rowe et al., 603-611 (2003).
Statistical Procedures for Bioequivalence Studies Using a Standard Two-Treatment Crossover Design, 13 pages (1992).

\* cited by examiner

METHOD FOR THE PRODUCTION OF A MEDICAMENT CONTAINING TADALAFIL

CROSS REFERENCE TO RELATED APPLICATIONS

This application is the U.S. National Stage of International Application No. PCT/EP2008/005066, filed Jun. 23, 2008, which claims the benefit of German Patent Application No. 10 2007 028 869.9, filed Jun. 22, 2007, each of which is hereby incorporated by reference.

The present invention relates to a method for the production of a pharmaceutical containing tadalafil, in which tadalafil is mixed with suitable excipients and is heated to a temperature from approx. 150° C. to approx. 200° C.

Tadalafil (IUPAC name: (6R,12aR)-6-(1,3-benzodioxol-5-yl)-2-methyl-1,2,3,4,6,7,12,12a-octahydropyrazino [2,1 :6,1]pyrido[3,4-b]indole-1,4-dione) belongs to the group of PDE-V (phosphodiesterase V) inhibitors, used as oral formulation for the treatment of erectile dysfunction (see e.g. WO01/08688). Tadalafil can be manufactured for example according to Daugan A. et al. (2003) J. Med. Chem., 46, 4533-4542, in which it is designated as (6R,12aR)-2,3,6,7, 12,12a-hexahydro-2-methyl-6-(3,4-methylene dioxyphenyl) pyrazino [2',1': 6,1]pyrido[3,4-b]indole-1,4-dione.

Tadalafil is sparingly soluble in water; according to WO 01/08687 it is only soluble in water to about 2 µg/ml. So that oral formulations have a high enough bioavailability even though the active substance is sparingly soluble, improvement of solubility is required.

EP 1 269 994 A2 describes so-called concentration improving polymers, for obtaining an improvement in the solubility of active substances.

WO 96/38131 describes a method of production of a solid dispersion, which contains a sparingly soluble active substance. The solubility of the active substance is said to be improved by coprecipitation. Tests on release of the active substance tadalafil have shown, however, that tablets that contain the coprecipitates release the active substance more slowly than tablets containing pure active substance. Moreover, in coprecipitates there are also proportions of tadalafil particles that are not embedded in the solid material, but are free. These free particles dissolve more quickly than the particles embedded in the coprecipitate. This may possibly lead to undesirable, bimodal release of the tadalafil. Furthermore, coprecipitates are not easily reproducible, i.e. large-scale production is complicated.

Another possibility for improving the solubility of sparingly soluble active substances is to increase the surface area of the particles of active substance by grinding or micronizing, as disclosed in WO 01/08688 or WO 01/08686. Oral formulations with rapid release are known from WO01/08688. The desired solubility or release could be achieved by reducing the tadalafil particle size to below 40 µm. Grinding or micronizing of active substances can, however, have disadvantages. Micronized particles tend to form agglomerates. This results in particle sizes that are difficult to define, and accordingly solubility that is difficult to define. A possible additional electrostatic charge on the active substance also has an adverse effect on processability. Another possible disadvantage is poor flowability of the ground active substance. Especially if tablets are to be compressed or capsules are to be filled, further processing steps, e.g. granulation, are necessary. Although the particles are small, it is often necessary to add a lot of surfactant to obtain adequate solubility.

Soft capsules made of gelatin, which are filled with a tadalafil solution, are known from WO 01/08687. The solvent for tadalafil is a mixture of PEG (polyethylene glycol) 400 NF LA and polypropylene glycol. Alternatively the capsules can be filled with a tadalafil suspension. Soft capsules made of gelatin are also known from WO 00/66099, using exclusively PEG 400 NF as solvent for the active substance. However, soft gelatin capsules have the disadvantage that filling is complicated. For example, special machines and strictly climate-controlled manufacturing rooms are required. In contrast, hard capsules can be filled relatively easily with standard capsule filling machines, equipped with feed systems for semi-solid substances instead of powder feed systems. Apart from gelatin as capsule material, it is also possible to use cellulose-based materials.

The problem to be solved by the present invention was therefore to provide a method for the production of a pharmaceutical containing tadalafil, in which the aforementioned disadvantages and in particular the difficult solubility of tadalafil are essentially avoided or overcome.

Surprisingly, it was found that tadalafil could be processed very well at elevated temperatures as a solid or semi-solid solution and higher concentrations or proportions of active substance in the formulation could be reached than was described for example in WO 01/08687.

The object of the present invention is therefore a method for the production of a pharmaceutical containing tadalafil, in which tadalafil is mixed with one or more suitable excipients and is heated to a temperature from approx. 100° C. to approx. 200° C., preferably approx. 150° C. to approx. 200° C., in particular approx. 200° C. In general, the lowest temperature is above the softening point of the corresponding excipient.

The term "approx." means according to the present invention generally ±5% and in particular ±2% of the respective physical quantity.

The term "excipient" generally comprises all common pharmaceutical excipients.

On the basis of the method according to the invention, the aforementioned disadvantages can essentially be overcome, as tadalafil was in the form of solid or semi-solid solutions. Solid solutions are characterized in that they are transparent and solid. Semi-solid solutions are characterized in that they are transparent and paste-like, i.e. not liquid. The solutions are accordingly viscous or highly viscous (like honey). The term transparent means that the tadalafil, which is usually in the form of white powder, is dissolved in the suitable excipient.

With solid and semi-solid solutions, basically there are no agglomerates, as the active substance is distributed in a suitable polymer as a molecular dispersion. This has the advantage that little or no surfactant is required. With solid and semi-solid solutions there is also no electrostatic charge. In addition, generally with solid solutions, the dissolution, forming of the melt and granulation take place in one process step, producing granules, pellets or microparticles with very good flowability, which are then compacted. With semi-solid solutions, dissolution and thickening can also take place in one step, followed by capsule filling.

Solid and semi-solid solutions have the further advantage, over coprecipitate powders, that no organic solvents are required. The method according to the invention is therefore environmentally friendly. Solvent recovery is not necessary. There is also, for example, no risk of solvent residues in the product and no explosion risk. The process steps are also considerably fewer and shorter, reducing the risk of degradation of the active substance during processing. Moreover, compared with coprecipitate powders, ground extrudates have better flow properties, ensuring better constancy of metering in tableting and capsule filling.

In a particular embodiment, the mixture is heated for up to approx. 2 hours, e.g. approx. 1 hour to approx. 3 hours, in particular approx. 1.5 hours to approx. 2.5 hours, quite especially approx. 2 hours, to achieve substantially complete melting of the excipients. This heating can be carried out in an ordinary stove. When a homogenizer is used, the heating time can even be much less than one hour, and when an extruder is used, the heating time can be approx. 1 minute to approx. 5 minutes.

The following have proved particularly suitable as excipients or solvents according to the present invention: polyethylene glycol (PEG), copovidone, a polyoxyethylene glycol monostearate, glycerol-polyethylene glycol-ricinoleate, polyvinyl-pyrrolidone and/or vinylpyrrolidone-vinyl acetate copolymer. PEG is selected in particular from PEG 200, PEG 400, PEG 600, PEG 800, PEG 1500, PEG 4000, PEG 6000, PEG 8000, PEG 10000 and/or PEG 20000, preferably from PEG 400, PEG 4000, PEG 6000 and/or PEG 20000 and in particular from PEG 400 and/or PEG 4000. The polyvinylpyrrolidone preferably has a molecular weight of approx. 40000 and the vinylpyrrolidone-vinyl acetate copolymer preferably has a molecular weight of approx. 60000. Other suitable excipients can also be added in addition to the aforementioned excipients.

Heating can advantageously also take place in an extruder, so that a homogeneous extrudate of active substance and excipient or solvent is obtained. Extrusion according to the invention preferably takes place at a discharge pressure from approx. 10 bar to approx. 100 bar, preferably from approx. 20 bar to approx. 100 bar, in particular from approx. 20 bar to approx. 50 bar. In particular, it is advantageous if the extruder has a temperature gradient from approx. 20° C. (inlet temperature) to approx. 200° C. (outlet temperature). For example, the following temperature gradients (approx. values) are advantageous, especially when vinylpyrrolidone-vinyl acetate copolymer preferably with a molecular weight of approx. 60000 is used as excipient:

Gradient 1: 20-50-100-150-160-160-200° C. preferably with approx. 50 bar discharge pressure or in particular
Gradient 2: 20-50-100-150-200-200-200° C. preferably with approx. 20 bar discharge pressure.

Depending on the extruder, extrusion die, screw configuration and/or material throughput, other parameters can be employed to achieve the same result, i.e. a transparent solution of tadalafil in the suitable excipient or the suitable excipient mixture.

The following excipients or solvents have proved to be especially advantageous for the extrusion process according to the invention: polyvinylpyrrolidone and/or vinylpyrrolidone-vinyl acetate copolymer, in particular polyvinylpyrrolidone with a molecular weight of approx. 40000 and/or vinylpyrrolidone-vinyl acetate copolymer with a molecular weight of approx. 60000.

With the method according to the invention, even higher proportions of tadalafil in the solid or semi-solid solution could surprisingly be obtained than were previously known. The proportion of tadalafil in the solid or semi-solid solution or in the extrudate can therefore be, according to the invention, approx. 2 wt. % to approx. 15 wt. %, preferably approx. 3 wt. % to approx. 10 wt. %, in particular approx. 5 wt. % to approx. 10 wt. %, and quite especially approx. 7.5 wt. % to approx. 10 wt. %. According to the present examples, in the extrusion process according to the invention approx. 7.5 wt. % tadalafil could be dissolved, otherwise even 10 wt. % tadalafil.

In accordance with the present invention, oral pharmaceutical formulations of tadalafil can be produced according to the present examples. In particular, pharmaceutical formulations were advantageous that contained, as further pharmaceutical excipients, Ludipress® or Kollidon®, in particular Kollidon® CL, or mixtures of Avicel®, in particular Avicel© PH 102, and Primojel®; of Avicel and Kollidon®, in particular Kollidon® CL; of Fujicalin® and Kollidon®, in particular Kollidon® CL; of L-HPC and LH11 and of Primojel® and Ac-Di-Sol®. Surprisingly, the pure extrudate of tadalafil and Kollidon® VA 64 was especially advantageous, as in this case the active substance was released the fastest.

Another object of the present invention is therefore also a pharmaceutical containing a solid or semi-solid solution of tadalafil, which can be produced by the method according to the invention, as described above in more detail. In particular the solid solution of tadalafil is produced by extrusion. The pharmaceutical therefore contains a solid or semi-solid solution of tadalafil, with preferably 80% of the tadalafil being released in vitro after 8-120 minutes, in particular after 20 minutes. The pharmaceutical is for example in the form of a tablet or a capsule, advantageously without further pharmaceutical excipients. The capsule is in particular a hard capsule, based e.g. on gelatin or HPMC.

The dose of active substance for oral use in humans is generally in the region of approx. 1-20 mg per day.

The following examples aim to explain the invention further, without limiting it.

EXAMPLES

Pharmaceutical Excipients and Abbreviations

Ac-Di-Sol® (FMC Corp.): croscarmellose (crosslinked sodium carboxymethylcellulose)

Aerosil® (Degussa GmbH) finely dispersed, hydrophilic silica

Avicel® (102/200; FMC Corp.): microcrystalline cellulose

Cellactose® (Molkerei Meggle Wasserburg GmbH & Co. KG): spray-dried mixture of 75% alpha-lactose monohydrate and 25% cellulose powder Cetiol® (Cognis GmbH): oleic acid oleyl ester CMC: carboxymethylcellulose Cremophor® EL (BASF AG): glycerol-polyethylene glycol ricinoleate DEP: diethyl phthalate DBS: dibutyl sebacate Emdex® (J. Rettenmaier & Söhne GmbH & Co. KG): malto-dextrin with 93-99% dextrose Eudragit® (Röhm & Haas GmbH): acrylic polymer Flowlac® (Molkerei Meggle Wasserburg GmbH & Co. KG): spray-dried alpha-lactose monohydrate Fujicalin® (Fuji Chemical Industry Co., Ltd): calcium hydrogen phosphate dihydrate Gelucire® (Gattefossé): semi-synthetic glycerides based on hydrogenated vegetable oils GMS: glycerol monostearate HPMC: hydroxypropyl methylcellulose Klucel® (Hercules Inc.): hydroxypropylcellulose Kollidon® CL (BASF AG): crospovidone (crosslinked polyvinylpyrrolidone)

Kollidon® VA 64 (BASF AG): copovidone (copolymer of vinylpyrrolidone and vinyl acetate; average molecular weight 60000±15000)

Kollidon® 30 (BASF AG): polyvinylpyrrolidone with a molecular weight of approx. 40000

Labrafil® (Gattefossé): transesterified and polyethoxylated, non-ionogenic triglycerides L-HPC (Shin-Etsu Chemical Co., Ltd): low-substituted hydroxypropylcellulose Lubritab® (Penwest Pharmaceuticals Co.): hydrogenated vegetable oil Ludipress® (BASF AG): composition comprising lactose monohydrate (approx. 93.4%), Kollidon® 30 (polyvinylpyrrolidone with a molecular weight of approx. 40000; approx. 3.2%), Kollidon® CL (crosslinked polyvinylpyrrolidone; approx. 3.4%) and water (≤6%)

Lutrol® (BASF AG): PEG

Microcelac® (Molkerei Meggle Wasserburg GmbH & Co. KG): spray-dried composition of microcrystalline cellulose (25%) and alpha-lactose monohydrate (75%)

Miglyol® (SASOL Germany GmbH): caprylic-capric acid triglyceride

PEG: polyethylene glycol with the corresponding molecular weight of e.g. 4000, 6000, 8000 and 20000

Pharmacoat® (Shin-Etsu Chemical Co., Ltd): hydroxypropyl methylcellulose

Pluronic® (BASF AG): polyoxyethylene-polyoxypropylene block polymer

Povidone: polyvinylpyrrolidone

Primojel® (Avebe B. A.): disintegrant based on sodium carboxymethylcellulose and starch PRUV® (JRS Pharma GmbH & Co. KG): sodium stearyl fumarate PVA: polyvinyl alcohol PVP: polyvinylpyrrolidone PVP-VA: copolymer of vinylpyrrolidone and vinyl alcohol SDS: sodium dodecylsulfate Solutol® (BASF AG): diethylene glycol monoethyl ether Tagat® (Goldschmidt AG): polyoxyethylene glycol monostearate TEC: triethyl citrate Example 1

Dissolution Tests of Tadalafil in Polymer Melts 0.5 g of tadalafil was mixed (homogenized) with 4.5 g of a polymer and heated for two hours in a stove to 200° C. Then it was left to cool to room temperature (1 hour). The proportion of active substance was 10 wt. %.

As a result of the dissolution tests, it was established that, in these conditions, tadalafil dissolved best in PEG 4000, PEG 6000, PEG 8000, PEG 20000 and Kollidon® VA64, dissolution being best with PEG 4000 (Lutrol® 4000 P). This was followed by Kollidon® VA64. PEG 6000, PEG 8000 (Lutrol® 8000 P) and PEG 20000 were still suitable.

Example 2

Dissolution Tests of Tadalafil in Liquid Polymers 1. 0.5 g of tadalafil was mixed with 4.5 g of a liquid excipient and treated with ultrasonic for two hours. Tadalafil remained undissolved in these conditions. Even heating to 80° C. for two hours did not produce any dissolution of the active substance.
2. In another experiment, 0.5 g of tadalafil was mixed with 4.5 g of a liquid excipient (proportion of active substance: 10 wt. %) and heated in a stove to 200° C. for two hours. Then it was left to cool to room temperature (1 hour).

As a result of these dissolution tests, it was established that under these conditions tadalafil dissolved best in Tagat®, PEG 400 and Cremophor® EL, with PEG 400 once again showing the best result.

Example 3

Melt Extrusion

For melt extrusion, 92.5 wt. % Kollidon® VA 64 and 7.5 wt. % tadalafil were mixed. Then they were mixed for five minutes in a Turbula T10B mixer and then at 1000 rpm in a Quadro Comil U5 mill at 1000 rpm sieved on a 1000 μm sieve. Then it was mixed again for 30 minutes in the Turbula T10B mixer.

Depending on the mixture, extrusion was carried out at an outlet temperature of 60-200° C. and a discharge pressure of 10-100 bar. The extruder had 7 individually heatable barrels, in which two screws transported the material from the inlet to the discharge nozzle. Barrel 1 is the inlet, where the powder mixture is fed in. Barrel 7 is the outlet, i.e. the extrusion die. The barrels were preheated for several hours before use. Various temperature gradients were set for extrusion, and the following two proved to be especially optimal:

a: 20/50/100/150/160/160/200° C.; resultant pressure ~50 bar
b: 20/50/100/150/200/200/200; resultant pressure ~20 bar In the selected conditions, extrudates were obtained in the form of strands with a diameter of 1.0 to 1.5 mm, which were cooled to room temperature and were then ground in two steps. The average particle size was approx. 1000 μm. Then the transparency of the products was investigated. It was found that the above temperature gradients led to transparent products. It was thus a solid solution of tadalafil in Kollidon® VA 64.

Example 4

Stability of the Extrudates

Extrudate b from example 3 was stored at 40° C. for four weeks, to investigate the stability of tadalafil. The test showed that with respect to chemical purity and release of tadalafil from the extrudate, essentially no difference was found between the stored extrudate and the non-stored extrudate directly after extrusion.

Example 5

Production of Tablets from Extrudate

Extrudate b from example 3 was ground in a Comil and sieved. Then it was mixed with excipients and the mixture was compressed to 340 mg tablets. Ground extrudate, sieved on a 1000 μm sieve, was used for formulations 1A-1H. For formulations 2A-2F, the ground extrudate was sieved first on an 800 μm sieve, then on a 500 μm sieve.

TABLE 1

| Formulation | Excipients | Proportion of tadalafil by weight (%) |
|---|---|---|
| 1A | Avicel ® 200 (8%) Flowlac ® (5%) Fujicalin ® (8.1%) Magnesium stearate (0.5%) | 78.4 |
| 1B | Microcelac ® (21.1%) Magnesium stearate (0.5%) | 78.4 |
| 1C | Kollidon ® VA 64 (8%) Flowlac ® (5%) Primojel ® (4.1%) Lubritab ® (4%) Magnesium stearate (0.5%) | 78.4 |
| 1D | Ludipress ® (21.1%) Magnesium stearate (0.5%) | 78.4 |
| 1E | Kollidon ® CL (21.1%) Magnesium stearate (0.5%) | 78.4 |
| 1F | Cellactose ® (21.1%) Magnesium stearate (0.5%) | 78.4 |
| 1G | Avicel ® PH 102 (16.1%) Primojel ® (5%) Magnesium stearate (0.5%) | 78.4 |
| 1H | Emdex ® (21.1%) Magnesium stearate (0.5%) | 78.4 |

TABLE 1-continued

| Formulation | Excipients | Proportion of tadalafil by weight (%) |
|---|---|---|
| 2A | Ludipress ® (16.4%) Sodium stearyl fumarate (0.3%) | 83.3 |
| 2B | Avicel ® 101 (11.4%) Kollidon ® CL (5%) Sodium stearyl fumarate (0.3%) | 83.3 |
| 2C | Kollidon ® CL(10.8%) Sodium stearyl fumarate (0.3%) | 88.9 |
| 2D | Fujicalin ® (5.8%) Kollidon ® CL (5%) Sodium stearyl fumarate (0.3%) | 88.9 |
| 2E | L-HPC LH11 (10.8%) Sodium stearyl fumarate (0.3%) | 88.9 |
| 2F | Primojel ® (5.4%) Ac-Di-Sol ® (5.4%) Sodium stearyl fumarate (0.3%) | 88.9 |

Tablets 1D and 1G and 2A to 2F showed the best (mechanical) stability.

Example 6

Production of a Quick-Release Hard Capsule with a Solid Tadalafil Solution

A melt-extrudate of active substance (1) and a polymer (2), e.g. Kollidon® VA64, Kollidon® 30, some other PVP polymer or a polymer instead of PEG or HPMC, is ground to any desired particle size distribution and optionally sieved. Optionally, the granules can be coated with further excipients (3), e.g. magnesium stearate, talc and/or colloidal silica. Capsules (4), e.g. hard capsules based on gelatin or HPMC, are then filled with the granules. Optionally, a solubility promotor, e.g. SDS, can be added before or after extrusion. A suitable hard capsule with an amount of active substance of 20 mg tadalafil has the following composition:

TABLE 2

| No. | Constituent | Function | Proportion (approx.) |
|---|---|---|---|
| 1 | Tadalafil | Active substance | 5-10% |
| 2 | Copovidone | Solid solvent | 85-95% |
| 3 | Magnesium stearate Talc Colloidal SiO$_2$ | Lubricant, flow improver | 0-5% |
| 4 | Hard capsules of gelatin or HPMC | Envelope | |

Example 7

Production of a Quick-Release Tablet with a Solid Tadalafil Solution

A melt-extrudate of active substance (1) and a polymer (2), e.g. Kollidon® VA64, Kollidon® 30, some other PVP polymer or a polymer instead of PEG or HPMC, is ground to any desired particle size distribution and optionally sieved. Then the grains are mixed with other excipients (3), e.g. cellulose, cellulose derivatives, starches, starch derivatives, PVP, lactose, sugars or sugar alcohols, PEG, calcium sulfate, calcium phosphate, carrageenan, kaolin and/or silica, and then a lubricant, e.g. sodium stearyl fumarate, magnesium stearate, stearic acid, hydrogenated vegetable oils, ethylene oxide; glycerol mono-, di- or tri-stearates, talc and/or SDS was added. The mixture was then compressed to tablets and coated with an aqueous or organic dispersion of further excipients and pigments (4)-(7). These further excipients are e.g. HPMC, polymethacrylates, PVA, PVP, PEG, CMC and/or copolymers of PVA, PVP and PEG as coating agent (4), dibutyl sebacate, PEG, propylene glycol, TEC, DBT and/or DEP as plasticizer (5) and stearic acid, magnesium stearate, stearic acid, hydrogenated vegetable oils, ethylene oxide; glycerol mono-, di- or tri-stearates, talc and/or SDS as moisture protection against sticking (6). Optionally, a solubility promotor, e.g. SDS, can be added before or after extrusion. A suitable hard capsule with an amount of active substance of 20 mg tadalafil has the following composition:

TABLE 3

| No. | Constituent | Function | Proportion (approx.) |
|---|---|---|---|
| 1 | Tadalafil | Active substance | 3-8% |
| 2 | Copovidone | Solid solvent | 20-80% |
| 3 | Excipients | Fillers, binders, disintegrants, flow improvers, lubricants | 20-80% |
| 4 | HPMC, polymethacrylate | Coating materials | Coating: 1-5% |
| 5 | Dibutyl sebacate | Plasticizer | |
| 6 | Stearic acid | Moisture protection against sticking | |
| 7 | Iron oxides | Pigments | |

Example 8

Production of a Capsule with a Semi-Solid Solution of Tadalafil

The active substance is dissolved in a heated excipient (2), e.g. PEG 600, Tagat® and/or Cremophor® EL with heating and optionally ultrasonic treatment, then mixed with an excipient (3), e.g. Aerosil® 200 or silica, hydroxyethylcellulose or other cellulose ethers, mixed in a homogenizer suitable for semi-solid substances and cooled. The semi-solid mass is filled in hard capsules by means of a capsule filling machine for semi-solid substances. Optionally, a solubility promotor, e.g. SDS, can be added before or after extrusion. A suitable hard capsule with an amount of active substance of 20 mg tadalafil has the following composition:

TABLE 4

| No. | Constituent | Function | Proportion (approx.) |
|---|---|---|---|
| 1 | Tadalafil | Active substance | 2-10% |
| 2 | PEG 600 | Liquid solvent | 50% |
| 3 | Silica | Thickener | 10-50% |
| 4 | Hard capsules of gelatin or HPMC | Envelope | |

Instead of silica, it is also possible to use cellulose or HPC as thickener.

Example 9

Active Substance Release Tests

Tests for the release of tadalafil were carried out in 1000 mL water (pH 7; 0.5% SDS) at 37° C. and 50 rpm (method according to US Pharmacopoeia, Apparatus II).

In vitro release tests with tablets 1D and 1G showed that 80% of the active substance was released after approx. 50-60 minutes (1D) or after approx. 120 minutes (1G). However, the pure granules from extrudate b from example 3 showed much quicker in vitro release than the aforementioned tablets, as 80% of the active substance tadalafil was already released after approx. 8-10 minutes.

It is possible, by varying the excipients, to influence the release of a composition with extrudate so that 80% of the tadalafil is released after approx. 20 minutes.

The invention claimed is:

1. A method for production of a pharmaceutical containing tadalafil, wherein tadalafil is mixed with a copolymer excipient comprising vinylpyrrolidone-vinyl acetate copolymer and is heated by melt extrusion in an extruder to a temperature from approximately 100° C. to approximately 200° C., wherein tadalafil is distributed, without agglomerates, in the copolymer excipient as a molecular dispersion, wherein the pharmaceutical containing tadalafil is a solid or semi-solid solution, wherein 80% of the tadalafil is released in vitro within 8-10 minutes.

2. The method as claimed in claim 1, wherein the vinylpyrrolidone-vinyl acetate copolymer has a molecular weight of approximately 60000.

3. The method as claimed in claim 1, wherein the proportion of tadalafil is approximately 2 wt. % to approximately 15 wt. % in the pharmaceutical.

4. The method as claimed in claim 2, wherein the temperature is from approximately 150° C. to approximately 200° C.

5. The method as claimed in claim 4, wherein the temperature is approximately 200° C.

6. A method for production of a pharmaceutical containing tadalafil, wherein tadalafil is mixed with a copolymer excipient comprising vinylpyrrolidone-vinyl acetate copolymer and is heated by melt extrusion in an extruder to a temperature from approximately 100° C. to approximately 200° C., wherein tadalafil is distributed, without agglomerates, in the copolymer excipient as a molecular dispersion, wherein the pharmaceutical containing tadalafil is a solid or semi-solid solution, wherein 80% of the tadalafil is released in vitro within 8-10 minutes, wherein the proportion of the molecularly dispersed tadalafil which is present in soluble form is approximately 2 wt. % to approximately 15 wt. %.

7. The method as claimed in claim 6, wherein the proportion of the molecularly dispersed tadalafil which is present in soluble form is approximately 7.5 wt % to approximately 10 wt. %.

8. The method as claimed in claim 6, wherein the proportion of the molecularly dispersed tadalafil which is present in soluble form is approximately 5 wt % to 10 wt. %.

* * * * *